United States Patent
Wakimura et al.

[11] Patent Number: 5,493,023
[45] Date of Patent: Feb. 20, 1996

[54] GRANULAR MELAMINE CYANURATE AND PREPARATION PROCESS THEREOF

[75] Inventors: Kazuo Wakimura; Tetsuo Yoshiyama; Hiroshi Kato; Yuri Kawano, all of Osaka, Japan

[73] Assignee: Mitsui Toatsu Chemicals, Inc., Tokyo, Japan

[21] Appl. No.: 160,174

[22] Filed: Dec. 2, 1993

[30] Foreign Application Priority Data

| Dec. 9, 1992 | [JP] | Japan | 4-329696 |
| Sep. 22, 1993 | [JP] | Japan | 5-236443 |
| Oct. 4, 1993 | [JP] | Japan | 5-247837 |

[51] Int. Cl.$^6$ ............ C07D 401/12; C07D 251/70
[52] U.S. Cl. ............ 544/198; 544/193; 544/196; 544/192; 544/200
[58] Field of Search ............ 544/196, 198, 544/200, 192, 193, 196

[56] References Cited

U.S. PATENT DOCUMENTS 4,282,359  8/1981  Guiliano et al. .............. 544/192
5,202,438  4/1993  Paul .............................. 544/198

FOREIGN PATENT DOCUMENTS

| 0507677 | 10/1992 | European Pat. Off. |
| 54-55587 | 5/1979 | Japan. |
| 54-55588 | 5/1979 | Japan. |
| 54-125690 | 9/1979 | Japan. |
| 1042174 | 9/1966 | United Kingdom ............ 544/192 |

OTHER PUBLICATIONS

Chemical Abstracts, vol. 92, No. 13, Mar. 31, 1980, Abstract No. 111070s., 1980.

*Primary Examiner*—Yogendra N. Gupta
*Attorney, Agent, or Firm*—Burns, Doane, Swecker & Mathis

[57] ABSTRACT

Melamine cyanurate is prepared by heating melamine powder and cyanuric acid powder at 250° to 500° C. substantially in the absence of any liquid medium. The melamine cyanurate can be obtained in a granular form when the heating is conducted subsequent to granulation of a mixture of both the powders.

9 Claims, 4 Drawing Sheets

GRANULAR MELAMINE CYANURATE AND PREPARATION PROCESS THEREOF

BACKGROUND OF THE INVENTION

1. Field of the Invention

This invention relates to melamine cyanurate and also to a process for its preparation. More specifically, the present invention is concerned with melamine cyanurate obtained by heating melamine and cyanuric acid without using any liquid medium, especially granular melamine cyanurate and also with a process for its preparation.

2. Description of the Related Art

Halogen-containing flame retardants have heretofore been used as one type of flame retardants for plastics. People have however become concerned with the toxicity of their combustion products to the human body, leading to an increasing demand for the change from low-halogen flame retardants to halogen-free flame retardants. Under these circumstances, substances containing a triazine ring, such as melamine and melamine cyanurate, are now under investigation as potential flame retardants. It is known to be possible to impart flame retardancy to urethane resins or polyamide resins by directly mixing melamine with urethane resins or melamine cyanurate with polyamide resins, both to a proportion of from several percent to 30 percent.

Melamine cyanurate has been prepared generally by separately dissolving melamine and cyanuric acid in water, mixing the resultant aqueous solutions to react them, collecting a precipitate of sparingly-soluble melamine cyanurate so formed, and then drying the melamine cyanurate.

To practice this process on an industrial scale, it is however accompanied inter alia by the following drawbacks: (1) the efficiency of preparation is low because the solubilities of melamine and cyanuric acid in water are too low to prepare thick aqueous concentrations, (2) the reaction product is in the form of fine particles so that its collection by filtration or the like is not easy, and (3) collected melamine cyanurate particles contain substantial water so that a long time is needed for drying them.

Industrial processes are disclosed in Japanese Patent Laid-Open Nos. 55587/1979 and 55588/1979. According to the process disclosed in the former patent publication, the reaction is carried out in the presence of water simply as a medium instead of reacting them in the form of aqueous solutions as described above. To melamine and cyanuric acid which are in the form of solids, respectively, water is added in an amount of 20–2,000 parts by weight per 100 parts by weight of the sum of the reactants, followed by their reaction under mixing or kneading. According to the process disclosed in the latter patent publication, on the other hand, melamine and cyanuric acid each of which has an average particle size not greater than 100 μm are formed into a uniform powder mixture. To the mixture, water is then added in an amount of 30–300% based on the mixture, followed by the reaction. These processes both require the addition of water for conducting the reaction, so that drying and grinding steps are needed subsequent to the reaction.

As a process making use of starting materials different from the above-described processes, Japanese Patent Laid-Open No. 125690/1979 discloses the process that urea and melamine, while still in solid forms, are mixed and heated to prepare melamine cyanurate. This process however requires an expensive corrosion-resistant material for the reactor. Further, when the mixture of urea and melamine is heated, they react with each other in a turbid melt while undergoing deammoniation. Therefore the resulting melamine cyanurate is in the form of a block and is not easy to handle. Its yield is not sufficient and, to obtain a high-purity product, further purification is indispensable.

SUMMARY OF THE INVENTION

An object of the present invention is to provide a process for the preparation of melamine cyanurate, said process being simpler in production steps and industrially superior compared with the conventional technology. Another object of the present invention is to provide powdery or granular melamine cyanurate having excellent properties.

To achieve the above object, the present inventors have proceeded with extensive research. As a result, it has been found that the reaction can still proceed even as a solid-solid reaction instead of a so-called solid-liquid reaction in the presence of a liquid medium provided that the reaction is effected under certain particular conditions, leading to the completion of the present invention.

In one aspect of the present invention, there is thus provided a process for the preparation of melamine cyanurate, characterized in that melamine powder and cyanuric acid powder are heated at 250° to 500° C. substantially in the absence of any liquid medium. Preferably, the melamine power and cyanuric acid powder can be heated after forming the mixture into granules.

In another aspect of the present invention, there is also provided powdery or granular melamine cyanurate obtained by the above process.

According to the present invention, melamine cyanurate can be prepared through steps simplified compared with the conventional processes. Further, the present invention can provide melamine cyanurate in a granular form so that the melamine cyanurate can be handled with ease.

DESCRIPTION OF THE DRAWINGS

The above and other objects, features and advantages of the present invention will become apparent from the following description and the appended claims, taken in conjunction with the accompanying drawings, in which:

DETAILED DESCRIPTION OF THE INVENTION AND PREFERRED EMBODIMENTS

Figure 1:
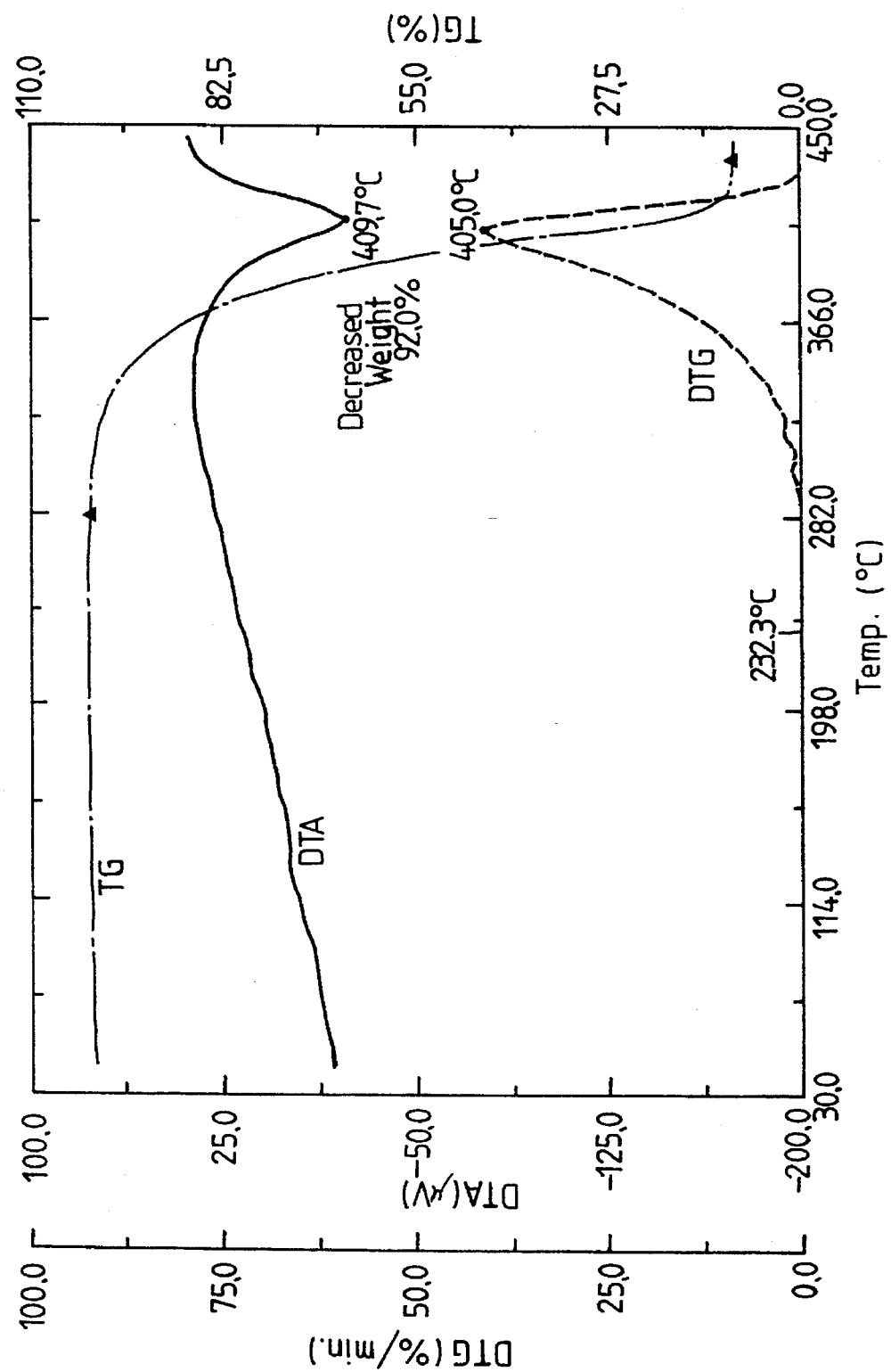
FIG. 1 shows a differential thermal analysis curve of melamine cyanurate obtained in Example 1 of the present invention.

The melamine powder employed in the present invention is available on the market. Illustrative of such commercial melamine powders include industrial melamine (product of Mitsui Toatsu Chemicals Inc.; melting point: 354° C., sublimation starting temperature: 210° C., average particle size: 20 μm).

The cyanuric acid powder is also generally available on the market, including for example that produced by Shikoku Kasei Corp. and available under the trade name of "ICA-P"

(melting point: 360° C., sublimation starting temperature: 230° C., average particle size: 80 μm).

Cyanuric acid has two tautomers, one being in the enol form and the other in the keto form. In chemistry, the enol form is called "cyanuric acid" whereas the keto form is called "isocyanuric acid". Cyanuric acid usable in the present invention, however, does not mean only the enol form but includes both the enol form and the keto form.

In the preparation process of the present invention, the melamine powder and the cyanuric acid powder may generally be used at a molar ratio of from 1:0.5 to 1:2.0. To obtain melamine cyanurate of high quality, their molar ratio can range from 1:0.9 to 1:1.1.

Although no particular limitation is imposed on the manner of mixing between the melamine powder and the cyanuric acid powder, it is preferred to mix them as uniformly as possible. Higher uniformity leads to a greater chance of contact between melamine molecules and cyanuric acid molecules, whereby the apparent reaction velocity increases. This can reduce the possibility of sublimation-related off-balancing in molar amount between the reactants, so that the yield is increased, the inclusion of unreacted started materials is reduced and the purity is improved.

As melamine powder and cyanuric acid powder to be supplied to a reactor, they may be used in a form mixed in advance before their introduction into the reactor or, after they are introduced into the reactor, they may be reacted under heat while being mixed.

It is desired that, when the melamine powder and the cyanuric acid powder are mixed together, the resulting mixture consists of particles not greater than 80 μm in diameter and has an average particle size not greater than 20 μm. To achieve this, it is possible to use, for example, melamine powder and cyanuric acid powder prepared in advance to avoid inclusion of particles greater than 80 μm and to have an average particle size not greater than 20 μm. Alternatively, the melamine powder and cyanuric powder can be mixed beforehand by a Henschel mixer, Nautamixer or the like into a mixture consisting of particles not greater than 80 μm in diameter and having an average particle size not greater than 20 μm. The mixture can be processed by a grinder such as a jet mill as needed.

According to the present invention, the reaction is considered to take place as a solid-solid or solid-gas reaction. Since the particle size of each solid starting materials affects the reaction velocity, it is suitable to comminute melamine powder and cyanuric acid powder to particles having diameters not greater than 80 μm and having an average particle size not greater than 20 μm as described above, preferably to particles having diameters not greater than 60 μm and an average particle size of from 0.5 to 10 μm, more preferably to particles having diameters not greater than 30 μm and having an average particle size of from 0.5 to 5 μm, before they are subjected to the reaction.

The melamine powder and the cyanuric acid powder, both having such particle sizes as mentioned above and still being in the form of solids, are introduced without any liquid medium into the reactor and then heated at 250°–500° C., preferably 250°–430° C., more preferably 300°–380° . When heated for about 10 minutes to about 4 hours, melamine cyanurate can be obtained readily. If the heating temperature does not reach 250° C., the reaction is extremely slow although it still proceeds. This results in a low yield of melamine cyanurate and the unreacted melamine and cyanuric acid remain to lower the purity. At temperatures above 500° C., the reaction product, i.e., melamine cyanurate, to say nothing of the melamine and the cyanuric acid as reactants, undergoes sublimation and complex reactions so that more impurities are formed, leading to lowered purity and yield. Incidentally, instead of air, an inert gas such as $N_2$ gas can be introduced into the reactor as needed.

In the above reaction, advance mixing and granulation of the melamine powder and the cyanuric acid powder permits smooth free-flow handling of the starting materials and the product and also preferred progress of the reaction.

Reasons for the above advantageous feature are not clear. It may however be elucidated that the mixture of the melamine powder and the cyanuric acid powder are compacted by its granulation and the reaction between melamine and cyanuric acid within each single granule would suppress sublimation of unreacted materials into the outside of the granule. Observed microscopically, it may be considered that the compaction increases the chance of contact between melamine molecules and cyanuric acid molecules and hence the apparent reaction velocity and the possibility of sublimation-related off-balancing in molar ratio between the reactants can thus be eliminated.

The melamine powder and the cyanuric acid powder, which make up a granular mixture of melamine powder and cyanuric acid powder in the present invention, can desirably be in the form of particles having diameters not greater than 80 μm and an average particle size not greater than 20 μm, preferably particles having diameters not greater than 60 μm and an average particle size of from 0.5 to 10 μm, more preferably particles having diameters not greater than 30 μm and an average particle size of from 0.5 to 5 μm. A mixture of melamine powder and cyanuric acid powder, which satisfy these requirements, is compressed by a granulator available on the market and, if necessary, ground, thereby preparing a granular mixture having an apparent grain size in a range permitting easy handling, preferably of from about 0.1 to 10 mm. The granular mixture may be prepared, for example, by compressing a mixture of melamine powder and cyanuric acid powder in a dry granulator and then grinding the resulting compact or by compressing a mixture of melamine powder and cyanuric acid powder in a semi-dry granulator, extruding the resulting mass through a die, chopping the extrudate at desired lengths and then drying the same.

Melamine cyanurate can be obtained either continuously or batchwise by heating the granular mixture of the melamine powder and the cyanuric acid powder as the starting materials, said granular mixture having been obtained as described above, at 250°–500° C. for 10 minutes to 4 hours still in a solid form without using any liquid medium. Incidentally, an inert gas such as $N_2$ gas can be introduced into the reactor as needed during the heating, so that air can be prevented from flowing into the reactor.

To apply the process of this invention to industrial production, it is not necessary to use any special autoclave as the reactor. However, a reactor having a hermetic structure of such an extent as preventing evaporation of at least the starting materials and the reaction product is employed. For example, the reactor may be an upright cylindrical reactor equipped with means for permitting heating of a reactor wall and having a cone-shaped lower section and rotary valves, one in a feed port for the starting materials and the other in a port through which the reaction product is withdrawn. In this case, a heating section inside the cylinder is used as a reaction zone, the reaction product is withdrawn continuously or batchwise from a bottom to achieve a predetermined residence time and the starting materials are fed from a top in amounts commensurate with the withdrawal of the reaction product.

When such a reactor is employed, it is particularly preferred to use the reactant mixture in a granular form. The granular mixture has good flowability, so that it can freely move or drop at a speed commensurate with the withdrawal and the supply without forming a bridge inside the reactor. As a consequence, the reactor can be operated smoothly without clogging. To promote conduction of heat, the reactor may internally be provided with such baffles that encourage both downward and sideward movement of the granular mixture. As has been described above, the present invention can obtain melamine cyanurate in a high yield at normal pressure without pressurizing the reactor.

The granular melamine cyanurate according to the present invention can be obtained by heating the above-described granular mixture of the melamine powder and the cyanuric acid powder at 250°–500° C., most preferably 300°–380° C. for 10 minutes to 4 hours. By suitably setting reaction conditions, the granular melamine cyanurate can be obtained with sufficiently high purity without purifying it specifically. The granular melamine cyanurate so obtained can therefore be used as a final product without any further processing. In general, its purity ranges from 98 to 99.9% while its bulk density ranges from 0.3 to 1.4 g/ml. The bulk density of the granular melamine cyanurate can be adjusted by changing the degree of compression at the stage of the granulation of the mixture of the starting materials, that is, of the melamine powder and cyanuric acid powder. Namely, the granular melamine cyanurate can be obtained with greater bulk density by increasing the degree of compression of the granular mixture. The granular melamine cyanurate may preferably have an apparent grain size of from about 0.1 to 10 mm. Since the granular melamine cyanurate can be obtained while substantially retaining the shape of the granular mixture of the starting materials, it is only necessary to control the apparent particle size to a desired value at the stage of the granular mixture of the starting materials.

Although the granular melamine cyanurate can be used as a final product without any further processing, its grain size can be adjusted by conventional grinding means such as a jet mill or a ball mill as needed in accordance with its use, whereby a final product can be provided. When employed as a flame retardant for a polyamide, for example, it is desired to disperse the melamine cyanurate in the polymer as evenly as possible. In such a case, the granular melamine cyanurate obtained in accordance with the process of the present invention can be used desirably in a form comminuted by a jet mill or the like.

Compared with powdery melamine cyanurate, the granular melamine cyanurate according to the present invention has a greater bulk density, scatters less, and sticks or deposits less on pieces of equipment. Therefore it is lost less during preparation and packaging and can be handled with ease. Further, it is more compact than powder so that costs required for transportation, storage and the like can be reduced.

The present invention will hereinafter be described more specifically by the following examples.

Example 1

Figure 3:
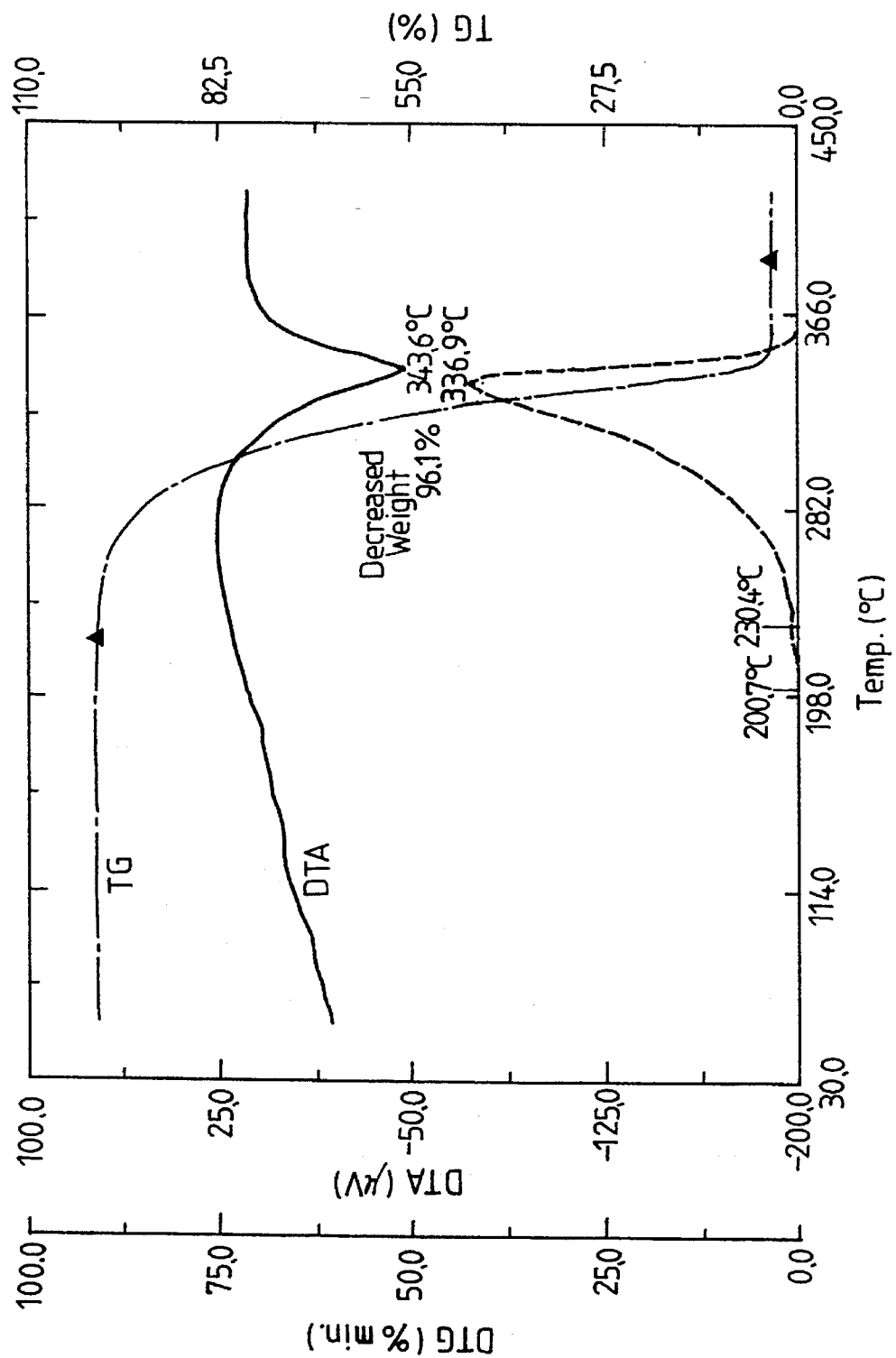
FIG. 3 illustrates a differential thermal analysis curve of melamine as a starting material.
Figure 4:
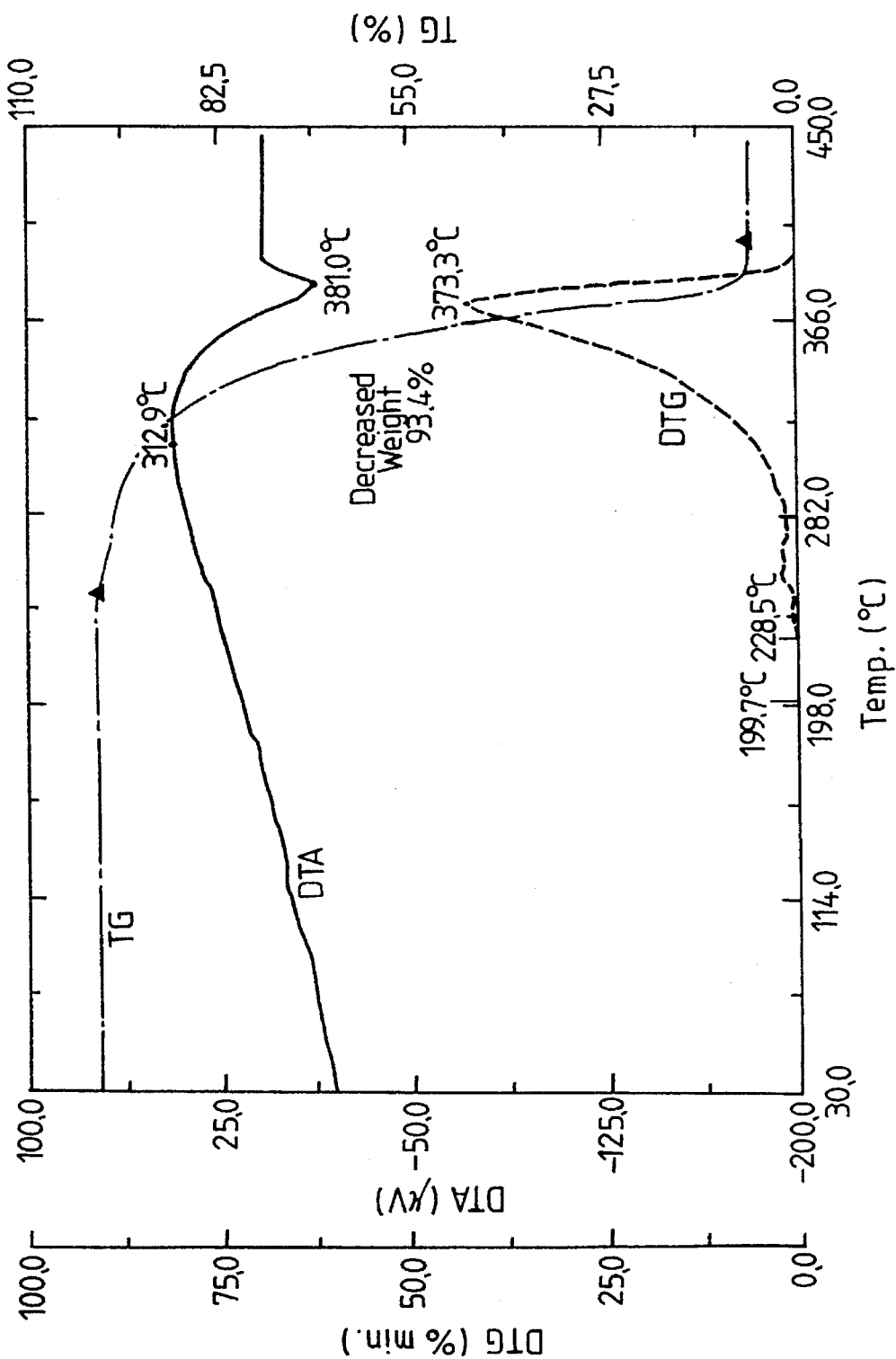
FIG. 4 depicts a differential thermal analysis curve of cyanuric acid as another raw material.

In a Henschel mixer having an internal capacity of 10 liters, 2.0 kg of industrial melamine (product of Mitsui Toatsu Chemicals Inc., melting point: 354° C., sublimation starting temperature: 210° C., average particle size: 20 µm) and 2.0 kg of cyanuric acid ("ICA-P", trade name; product of Shikoku Kasei Corp.; melting point: 360° C., sublimation starting temperature: 230° C., average particle size: 80 µm) were charged, followed by mixing at room temperature for 10 minutes. Using a jet mill, the mixture was continuously fed in its entirety at 33.4 kg/hr and room temperature so that 3.91 kg of a comminuted mixture were formed. The average particle size of the comminuted mixture was 3.94 µm (as determined based on volumes measured by the laser beam diffractometry). After 78.25 g of the comminuted mixture were placed in an evaporating dish, its surface was covered by an aluminum foil. The evaporating dish was then placed in an electric furnace, in which the comminuted mixture was heated at 350° C. for 1 hour to obtain 74.99 g of melamine cyanurate. Its yield, purity and average particle size were 95.8%, 99.2% and 4.83 µm, respectively. A differential thermal analysis curve of the melamine cyanurate so obtained is shown in FIG. 1. Incidentally, differential thermal analysis curves of the starting materials, that is, of the melamine and cyanuric acid are illustrated in FIGS. 3 and 4, respectively.

Example 2

The procedures of Example 1 were repeated except that the reaction was conducted using the mixture obtained after the mixing in the Henschel mixer without using the jet mill. As a result, the yield was 80.7% while the purity was 93.8%. The lower yield than that achieved in Example 1 is believed attributable to a greater particle size of the starting materials.

Comparative Example 1

In a similar manner to Example 1 except for the omission of the grinding by the jet mill, 2.0 kg of industrial melamine (product of Mitsui Toatsu Chemicals Inc., average particle size: 100 µm) and 2.0 kg of cyanuric acid ("ICA-P", trade name; product of Shikoku Kasei Corp.; average particle size: 80 µm) were reacted. The yield and purity were 14.2% and 38.7%, respectively.

Example 3

Using 78.58 g of the comminuted mixture obtained in Example 1, 77.45 g of melamine cyanurate were obtained in a similar manner to Example 1 except that the comminuted mixture was heated at 300° C. for 4 hours. The yield, purity and average particle size were 98.6% 99.1% and 6.21 µm, respectively.

Example 4

Placed in a 50 ml stainless steel autoclave which was designed to permit heating up to 500° C. were 6.3 g of industrial melamine (product of Mitsui Toatsu Chemicals Inc., average particle size: 20 µm) and 6.5 g of cyanuric acid ("ICA-P", trade name; product of Shikoku Kasei Corp.; average particle size: 3.1 µm) which had been comminuted beforehand by the jet mill. The contents were gradually heated to 350 ° C. under mixing. The contents were then maintained at 350° C. under mixing for further 1 hour, whereby 12.2 g of melamine cyanurate were obtained. The yield, purity and average particle size were 98.3%, 99.6% and 18.4 µm.

Comparative Example 2

The procedures of Example 4 were repeated except that 9 g of prilled urea (product of Mitsui Toatsu Chemicals, Inc.; melting point: 132° C.; average particle size: 1 mm) were reacted, in place of the cyanuric acid, with 4.5 g of the melamine at 300° C. As a result, melamine cyanurate was obtained in the form of a block. The yield and purity were 93% and 87.2%, respectively.

Example 5

In a Nautamixer (manufactured by Hosokawa Micron Corporation) having an internal capacity of 100 liters, 20.0 kg of industrial melamine (product of Mitsui Toatsu Chemicals Inc., melting point: 354° C., sublimation starting temperature: 210° C., average particle size: 20 μm) and 20.0 kg of cyanuric acid ("ICA-P", trade name; product of Shikoku Kasei Corp.; melting point: 360° C., sublimation starting temperature: 230° C., average particle size: 80 μm) were charged, followed by mixing at room temperature for 1 hour. After the resulting mixture was comminuted by the jet mill to reduce its average particle size to 3.24 μm, the thus comminuted mixture was formed into granules having an average grain size of 1 mm by a dry granulator ("PHARMAPACTER L2000/50P MODEL", trade name; manufactured by Hosokawa Micron Corporation).

Figure 2:
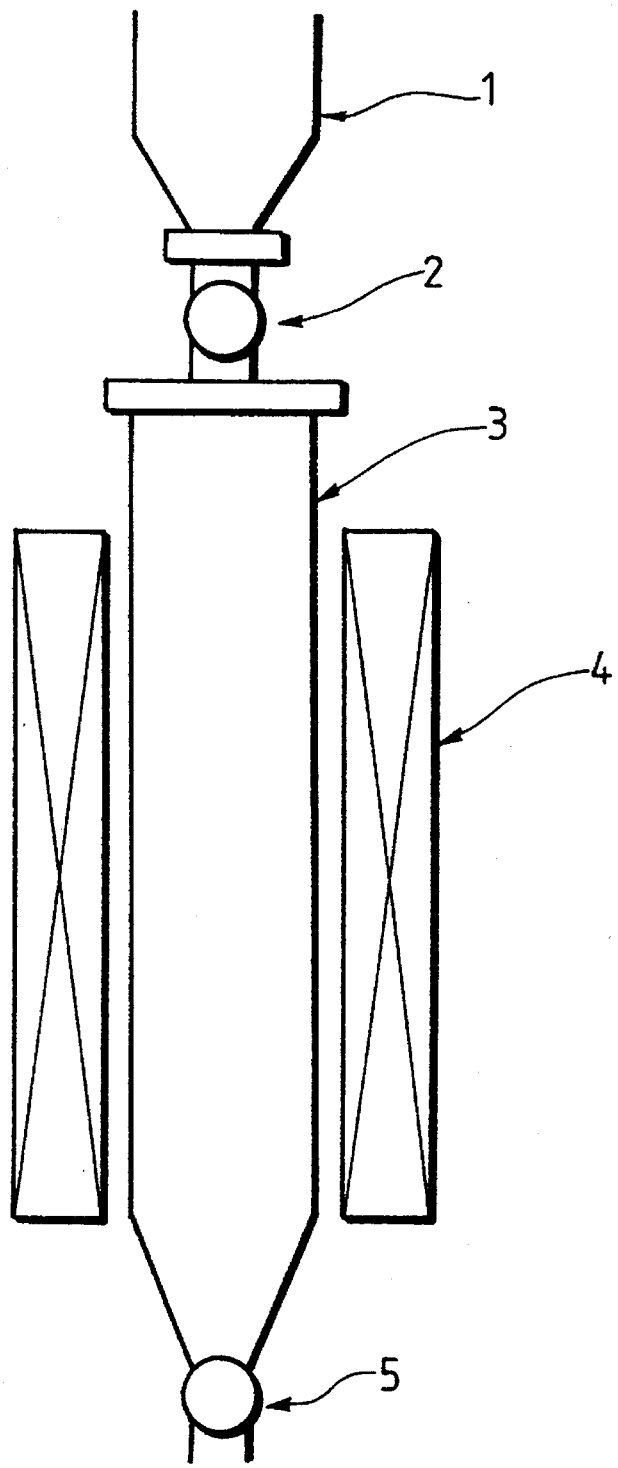
FIG. 2 is a simplified schematic cross-section of a reactor employed in Example 5 of the present invention.

From a top of an upright cylindrical reactor which is shown in FIG. 2 and was equipped with an internal thermometer and had a diameter of 2 inches and a length of 1 m, the granular mixture so obtained was then continuously fed at a rate of 1 liter per hour by using a rotary valve 2. From a bottom of the reactor 3, the reaction mixture was continuously withdrawn at substantially the same rate by using a rotary valve 5. During the operation, the reaction temperature inside the reactor was controlled at 350° C. while the residence time of the reaction mixture in a constant-temperature zone jacketed With a heater 4 was controlled at 1 hour.

The operation was continuously conducted for about 24 hours. During the operation, no trouble such as clogging occurred, thereby obtaining granular melamine cyanurate in a yield of 98.9%. Its purity and average grain size were 98.5% and 1 mm, respectively. After the end of the operation, the interior of the reactor was checked. Stuck or deposited powder was not observed. By grinding the thus-obtained granular product in a jet mill, a powdery product having an average particle size of 4.83 μm was obtained. As a result of a differential thermal analysis of the melamine cyanurate obtained after the grinding, a single peak was observed like the DTA curve shown in FIG. 1. The sublimation starting temperature was 290° C.

Comparative Example 3

The procedures of Example 5 were repeated except that the granulation was omitted and the powdery mixture was fed to the reactor as was. Withdrawal of the reaction mixture from the bottom of the reactor was not smooth. Six hours later, the bottom of the reactor was clogged so that the continuous operation became no longer feasible. It was caused because the powder formed a bridge inside the reactor.

Example 6

Five kilograms of the granular mixture obtained in Example 5 were charged in the reactor shown in FIG. 2 and were then heated at 350° C. for 2 hours. After completion of the reaction, the reaction mixture was withdrawn so that a granular product was obtained in an amount of 4.95 kg (yield: 99.0%, purity: 98.7%). The granular product was then ground by the jet mill as in Example 5, whereby a powdery product was obtained. The powdery product was subjected to a differential thermal analysis. As a result, the powdery product was found to have a similar peak as the DTA curve shown in FIG. 1.

Example 7

The procedures of Example 5 were repeated except that the reaction temperature and the residence time were changed to 400° C. and 30 minutes. The yield and purity were 95.7% and 99.3%, respectively. The product so obtained was subjected to a differential thermal analysis. As a result, the product was found to have a similar peak as the DTA curve shown in FIG. 1. The sublimation starting temperature was 295° C.

Example 8

The procedures of Example 5 were repeated except that the reaction temperature and the residence time were changed to 300° C. and 2 hours. The yield and purity were 99.2% and 98.2%, respectively. The product so obtained was subjected to a differential thermal analysis. As a result, the product was found to have a similar peak as the DTA curve shown in FIG. 1. The sublimation starting temperature was 288° C.

Comparative Example 4

The procedures of Example 5 were repeated except that the reaction temperature and the residence time were changed to 200° C. and 4 hours. Melamine cyanurate was not obtained practically. From the bottom of the reactor, the granular mixture of melamine and cyanuric acid as starting materials was discharged from the bottom of the reactor.

Example 9

A reaction was continuously conducted in a similar manner to Example 5 except for the use of a heated kneader-type reactor. The operation was carried out continuously for about 24 hours. During the operation, no trouble such as clogging occurred and the operation proceeded smoothly. The yield and purity were 98.5% and 98.3%, respectively.

What is claimed is:

1. A process for the preparation of melamine cyanurate, comprising heating melamine powder and cyanuric acid powder at 250° to 500° C. in the absence of any liquid medium wherein the melamine powder and the cyanuric acid powder individually have an average particle size of not greater than 20 μm.

2. A process of claim 1, wherein the melamine powder and the cyanuric acid powder are heated under mixing.

3. A process of claim 1, wherein a mixture of the melamine powder and the cyanuric acid powder is formed and then heated.

4. A process of claim 1, wherein a mixture of the melamine powder and the cyanuric acid powder has an average particle size not greater than 20 μm.

5. A process of claim 1, wherein a mixture of the melamine powder and the cyanuric acid powder is formed into granules and the granules are then heated.

6. A process of claim 5, wherein a mixture of the melamine powder and the cyanuric acid powder has an average particle size not greater than 20 μm.

7. A process of claim 5, wherein the granules have a grain size of from 0.1 to 10 mm.

8. A process of claim 5, wherein an upright reactor having a cone-shaped lower section is provided, the granules of the mixture of the melamine powder and the cyanuric acid powder are supplied to an upper section of the reactor and are then heated, and a reaction product is withdrawn from the lower section of the reactor.

9. A process of claim 5, wherein the granules of the mixture of the melamine powder and the cyanuric acid powder have been obtained by compressing the mixture.

* * * * *